Figure 1:
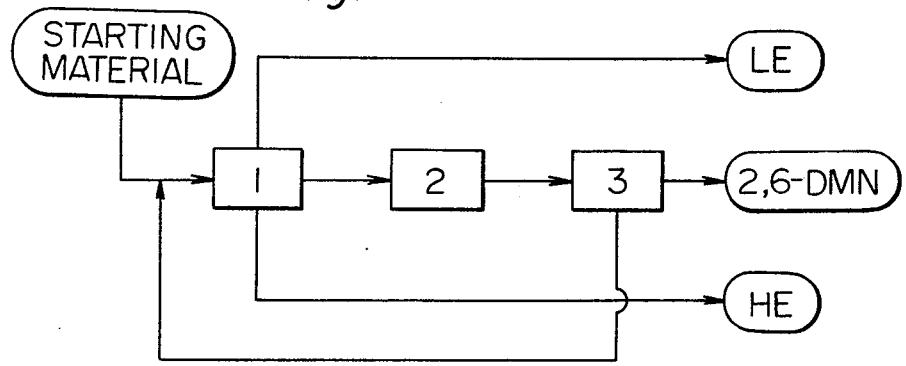

United States Patent [19]

Yokoyama et al.

[11] 3,957,896

[45] May 18, 1976

[54] PROCESS FOR PREPARING 2,6-DIMETHYLNAPHTHALENES

[75] Inventors: Seiichi Yokoyama; Takanori Urasaki; Michiyuki Tokashiki; Takeo Shima, all of Iwakuni, Japan

[73] Assignee: Teijin Limited, Osaka, Japan

[22] Filed: May 30, 1974

[21] Appl. No.: 474,718

[30] Foreign Application Priority Data

May 31, 1973 Japan................................ 48-60256

[52] U.S. Cl............................................. 260/668 A
[51] Int. Cl.²........................................ C07C 5/24
[58] Field of Search................................ 260/668 A

[56] References Cited
UNITED STATES PATENTS

| | | | |
|---|---|---|---|
| 3,243,469 | 3/1966 | Schneider...................... | 260/668 D |
| 3,775,498 | 11/1973 | Thompson...................... | 260/668 D |
| 3,781,375 | 12/1973 | Shima........................... | 260/668 D |

Primary Examiner—C. Davis
Attorney, Agent, or Firm—Sherman & Shalloway

[57] ABSTRACT

A process for preparing 2,6-dimethylnaphthalene by the selective isomerization of an isomeric mixture of dimethylnaphthalenes(DMN), characterized in that 1. the weight ratio of DMN of group A which includes 2,6-DMN, 1,6-DMN, and 1,5-DMN to other DMN (not belonging to group A) in the isomerization reactant is adjusted to not more than 12,
2. the weight percent of 2,6-DMN in the reaction product is adjusted to at least 27 based on the DMN of group A contained therein,
3. the disproportionation ratio D (weight percent) of other DMN (not belonging to group A) and the conversion G (weight percent) of DMN of group A to other DMN satisfy the relation expressed by $D \leq -0.9G + 6.76$, and
4. the residue in the crystallization step is recycled to the isomerization step.

10 Claims, 2 Drawing Figures

PROCESS FOR PREPARING 2,6-DIMETHYLNAPHTHALENES

This invention relates to a process for preparing 2,6-dimethylnaphthalene.

Dimethylnaphthalenes (DMN) have the following ten isomers.

Dimethylnaphthalenes of group A: 2,6-DMN, 1,6-DMN, 1,5-DMN

Dimethylnaphthalenes of group B: 2,7-DMN, 1,7-DMN, 1,8-DMN

Other dimethylnaphthalenes: 2,3-DMN, 1,3-DMN, 1,2-DMN

Of these, 2,6-DMN is very useful for commercial application since it can be a material for polyesters having superior physical and chemical properties after being converted to naphthalene-2,6-dicarboxylic acid.

There has been known a method for preparing such a 2,6-DMN which comprises intramolecularly rearranging the methyl groups of 1,5- and 1,6-DMN, inducing a main reaction expressed by the following equation

cooling the resulting reaction product, crystallizing 2,6-DMN utilizing the difference in solubility among the isomers, and thus separating it.

It is known that generally in the isomerization reaction of dimethylnaphthalenes, the intramolecular rearrangement of dimethylnaphthalenes occurs simultaneously with the intermolecular rearrangement of dimethylnaphthalenes. Accordingly, in the following reaction of intramolecularly rearranging the methyl groups of 1,5- or 1,6-DMN to obtain 2,6-DMN

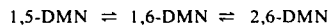

it is very difficult to perform the isomerization reaction completely selectively among the above three components alone, and although differing according to the reaction conditions, dimethylnaphthalenes other than those of group A which consist mainly of 2,7-DMN and 1,7-DMN, components having lower boiling points than DMN such as monomethylnaphthalenes (MMN), and/or components having higher boiling points than DMN such as trimethylnaphthalenes (TMN) are formed as by-products.

Of these by-products, the components having lower or higher boiling points than DMN, such as MMN and TMN, can be easily separated from the dimethylnaphthalenes of group A by a distillation method. However, it is extremely difficult to separate dimethylnaphthalenes not belonging to group A which consist mainly of dimethylnaphthalenes of group B from the desired dimethylnaphthalenes of group A by known means such as recrystallization or distillation.

In the commercial production of 2,6-DMN, for example, by intramolecularly rearranging the methyl groups of 1,5- and 1,6-DMN, cooling the resulting reaction product, and separating 2,6-DMN, it is advantageous to recycle the residue finally separated to an isomerization step and isomerizing it again. However, according to the above method, dimethylnaphthalenes not belonging to group A which consist mainly of dimethylnaphthalenes of group B are gradually accumulated in the reaction system, and as a result, the yield of the desired 2,6-DMN is markedly reduced or else the purity of the resulting 2,6-DMN is very much impaired. This is because in addition to the formation of dimethylnaphthalenes not belonging to group A as a result of the above isomerization reaction, dimethylnaphthalenes not belonging to group A come into the reaction as a result of recycling, or at times, fed into the reaction system as contained in the DMN isomeric mixture to be freshly supplied to the reaction system, for example, as contained in 1,5-DMN synthesized by a known method, with the result that the amount of dimethylnaphthalenes not belonging to group A present in the reaction system increases considerably.

It is an object of this invention therefore to solve this problem, and to provide a process for preparing high purity 2,6-DMN at a high yield and with commercial advantage.

In view of the above object of this invention, we have extensively investigated a process for preparing 2,6-DMN very easily and advantageously on a commercial scale, and finally found that 1. it is difficult to isomerize completely selectively a DMN isomeric mixture containing DMN of group A and other dimethylnaphthalenes (not belonging to group A) which consist mainly of dimethylnaphthalenes of group B. Although DMN not belonging to group A (which consists mainly of DMN of group B), MMN and TMN are mainly formed from the DMN of group A; and DMN of group A, MMN and TMN are mainly formed from dimethylnaphthalenes not belonging to group A (which consist mainly of those of group B), the proportion of the DMN of group A so formed from other dimethylnaphthalenes is greater than the proportion of the dimethylnaphthalenes not belonging to group A so formed from DMN of group A, 2. by-products such as MMN or TMN are formed from both of the DMN of group A and the DMN not belonging to group A in almost the same proportions, and 3. when the following definitions are provided with regard to the isomerization reaction product $$C_{26} = \frac{2,6\text{-DMN (weight)}}{2,6\text{-DMN (weight)} + 1,6\text{-DMN (weight)} + 1,5\text{-DMN (weight)}} \times 100$$

$$D = \frac{\text{Weight of by-products other than DMN, formed from DMN not belonging to group } A}{\text{Weight of the DMN not belonging to group } A \text{ which is contained in the isomerization reactant}} \times 100 \text{ (wt.\%)}$$

$$G = \frac{\text{Weight of DMN not belonging to group } A, \text{ formed from DMN of group } A}{\text{Weight of DMN of group } A \text{ contained in the isomerization reactant}} \times 100 \text{ (wt.\%)}$$

high purity 2,6-DMN can be prepared in a high yield by recycling at a certain rate the dimethylnaphthalenes not belonging to group A which consist mainly of DMN of group B and which are present in the isomerization reactant, prescribing the isomerization reaction conditions so that $C_{26}$, D and G are within certain specific ranges, and combining a crystallization step with a distillation step.

According to the present invention, there is provided a process for preparing 2,6-dimethyl naphthalene by the selective isomerization of a dimethyl naphthalene mixture, which comprises a step of isomerizing a mixture of dimethyl naphthalenes in the presence of a solid acid catalyst, a crystallization step of separating 2,6-dimethyl naphthalene from the resulting isomerized reaction mixture, and a distillation step of separating components having lower or higher components than dimethylnaphthalenes contained in the dimethylnaphthalene mixture at any desired stage of the process; characterized in that 1. the concentration of 2,6-dimethylnaphthalene in the isomerization reactant for the isomerization reaction is less than the thermodynamic equilibrium concentration, and the weight ratio of dimethyl naphthalenes of group A consisting of 2,6-dimethyl naphthalene, 1,6-dimethylnaphthalene and 1,5-dimethylnaphthalene to the dimethylnaphthalenes not belonging to group A is defined by $$\frac{\text{Weight of DMN of group } A}{\text{Weight of DMN not belonging to group } A} \leq 12$$

2. in said isomerization reaction, the concentration $C_{26}$ of 2,6-DMN in the reaction product expressed in percent by weight based on the DMN of group A satisfies the following equation $$C_{26} = \frac{2,6\text{-DMN (weight)}}{2,6\text{-DMN (weight)} + 1,6\text{-DMN (weight)} + 1,5\text{-DMN (weight)}} \times 100$$
$$27 \text{ (wt.\%)}$$

and the disproportionation ratio D of DMN not belonging to group A, which is the weight percent of said low boiling and/or high boiling components converted from DMN not belonging to group A during the reaction to DMN not belonging to group A present in the isomerization reactant, and the conversion G (weight percent) of DMN not belonging to group A converted from DMN of group A during the reaction to DMN of group A present in the isomerization reactant satisfy the following equation $$D \leq -0.9 G + 6.76 \text{ (wt.\%)}$$

and 3. the residue resulting from the separation of 2,6-dimethylnaphthalene in the crystallization step is recycled to the isomerization step to use it as a part of the starting material.

An embodiment of the isomerization step, crystallization step and distillation step used in combination in the present invention will be described by reference to the accompanying drawing which gives flow charts illustrating the embodiment of this invention.

Figure 2:
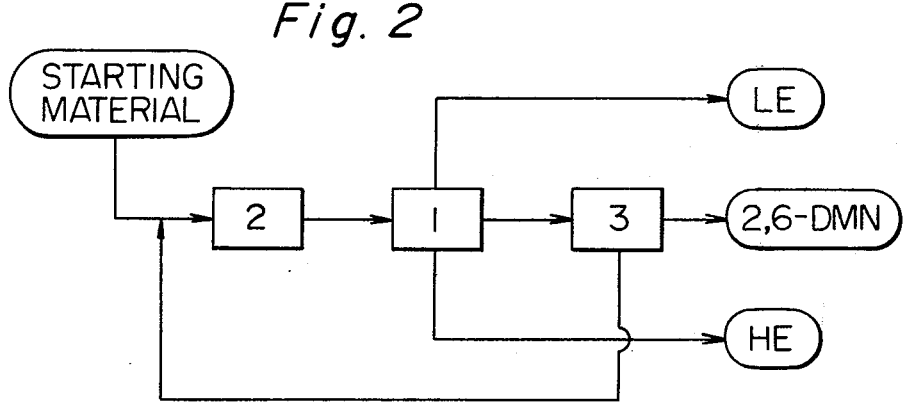

FIG. 1 shows an example in which the distillation step is provided before the isomerization step, and FIG. 2 shows an example in which the distillation step is provided between the isomerization step and the crystallization step.

At least one distillation step for separating low boiling components having a higher vapor pressure than the dimethylnaphthalenes contained in the processing system and/or high boiling components having a lower vapor pressure than the above dimethylnaphthalenes is provided before the isomerization step, or between the isomerization step and the crystallization step, or at any point during the recycling of the residue resulting from the separation of 2,6-DMN in the crystallization step to the isomerization step.

As one example, the provision of the distillation step before the isomerization step will be described by referring to the accompanying drawings, but the invention is not limited to this embodiment.

Referring to FIG. 1, the starting material to be freshly introduced into the processing system is mixed with a recycle flow of the residue resulting from the separation of 2,6-DMN in the crystallization step 3, and then enters the distillation step 1. This mixed flow contains low boiling components having a higher vapor pressure than DMN and/or high boiling components having a lower pressure than DMN which are formed by the isomerization reaction and contained in the recycle flow, or at times, these components come in as contained in the freshly introduced starting material. In the distillation step 1, these lower boiling and/or high boiling components in the mixed flow are separated and removed from the dimethylnaphthalenes.

In the distillation step 1, dimethylnaphthalenes containing DMN of group A as main components resulting from the separation of the low boiling and/or high boiling components are then fed into the isomerization step, and the reaction product obtained in this step is then fed into the crystallization step 3 where 2,6-DMN is separated and high purity 2,6-DMN is withdrawn.

The isomerization reaction catalyst to be used in the present invention may be any kind of solid acid catalyst obtained in nature or by synthesis. Examples of suitable solid acid catalysts are silica-alumina, silica-magnesia, silica-zirconia, silica-alumina-zirconia, fuller's earth, natural or synthetic mordenite, X-type zeolite, Y-type zeolite, A-type zeolite, and L-type zeolite. These catalysts may be substituted partly or wholly by hydrogen or metal. Or they may carry a metal of Group 8 of the periodic table, such as platinum or palladium thereon. Of these, the silica-alumina, natural or synthetic mordenite, X-type zeolite, Y-type zeolite, A-type zeolite, and L-type zeolite are preferred. The natural or synthetic mordenite, X-type zeolite, Y-type zeolite, and L-type zeolite are especially preferred, and the hydrogen form of mordenite and metal form of mordenite are most preferred. It is frequently preferred to use these catalysts together with carriers. Suitable carriers or binders are, for example, bentonite, fuller's earth, alumine, silica-alumina, and titanium oxide. Of these bentonite and fuller's earth are preferred.

Suitable metals for metal exchange of the above catalysts are, for example, Mg, Ca, Sr, Ba, Al, Ti, Zr, Cr, Mo, Mn, Re, Co, Ni, Pd, Zn, Cd, Fe and Be. Of these, Mg, Ca, Sr, Ba, Al, Cr, Mn, Co, Zn and Fe are preferred.

The ratio of exchange with hydrogen and/or metal is not particularly restricted, but preferably, it is at least 20%, and especially preferably at least 50%.

The isomerization reaction may be carried out either in the vapor phase or in the liquid phase.

The reaction apparatus to be used in this invention may be of any known type such as a fixed bed, moving bed, fluidized bed or liquid phase suspended bed. Generally, however, the use of a fixed bed is commercially preferred. The reaction temperature is not particularly limited, but can vary according to the type of the solid acid catalyst used. The isomerization reaction is carried out generally at 200° to 500°C. The reaction pressure and the partial pressure of dimethylnaphthalenes are neither restricted in particular, but are suitably selected according to the other reaction conditions.

A diluent may or may not be used. When it is used, it may be any inert diluent. Generally, the use of a diluent is preferred when the reaction is carried out in the vapor phase. Examples of the diluent are nitrogen gas, helium gas, carbon dioxide gas, and hydrogen gas. In the case of the liquid phase reaction, a diluent may or may not be used. Any diluents which are inert to the reaction and liquefiable can be used in this invention.

The rate of feeding the reactants is neither restricted in particular, but generally, the space velocity is at least 0.01 Kg/Kg-cat/hr, preferably 0.05 to 30 Kg/Kg-cat/hr.

The linear velocity is not restricted in particular. However, in the case of a fixed bed, the linear velocity is generally 0.1 to 200 cm$^3$/cm$^2$.sec. for a vapor phase reaction and at least 0.001 cm$^3$/cm$^2$.sec. for a liquid phase reaction, both on the basis of superficial column.

If desired according to the reaction conditions, additives such as water or steam can be used.

The material to be freshly fed into the processing system in FIG. 1 may have a dimethylnaphthalene mixture prepared by any method which contains 2,6-DMN in a concentration less than the thermodynamic equilibrium concentration and contains dimethylnaphthalenes not belonging to group A and consisting mainly of dimethylnaphthalenes of group B in a proportion of not more than 15% by weight, preferably not more than 10% by weight, especially preferably not more than 5% by weight. However, dimethylnaphthalenes consisting mainly of 1,5-DMN which can be obtained easily by cyclizing and dehydrogenating 5-o-tolyl-pentene-(2) obtainable by reacting o-xylene and butadiene that are readily available commercially are most conveniently used.

One novel aspect of this invention is that 2,6-DMN can be produced at a very high yield by performing the process while maintaining the disproportionation ratio D of dimethylnaphthalenes not belonging to group A and the conversion G of dimethylnaphthalenes of group A to those not belonging to group A within the above-specified ranges, controlling the amount of the recycle flow according to the amount of dimethylnaphthalenes of group A contained in the freshly fed material so that the ratio of dimethyl naphthalenes of group A to those not belonging to group A in the total feed supplied to the isomerization step becomes not more than 12 and thus the dimethylnaphthalenes not belonging to group A will be accumulated in the reaction system. The above conditions have been specified based on the fact that in the isomerization reaction of a DMN isomeric mixture, the ratio of dimethylnaphthalenes not belonging to group A which are to be formed from dimethylnaphthalenes of group A is less than that of dimethylnaphthalenes of group A to be formed from dimethylnaphthalenes not belonging to group A.

Since prior to the present invention, it was thought that when dimethylnaphthalenes not belonging to group A are accumulated in the reaction system, the yield of 2,6-DMN is reduced, and therefore, the ratio of DMN of group A to DMN not belonging to group A in the total feed should not be decreased, it is indeed surprising that in the present invention, high purity 2,6-DMN can be obtained in a high yield when the above ratio is maintained at not more than 12.

If the amount of the recycle flow of dimethylnaphthalenes not belonging to group A is reduced so that the ratio of DMN of group A to DMN not belonging to group A in the total feed supplied to the isomerization step is greater than 12, it is necessary to avoid intermolecular rearrangement and reduce the amount of DMN not belonging to group A to be freshly introduced into the processing system to the greatest possible extent. Otherwise, it would be necessary to reduce the yield $[(\eta_{26})_T(\%)]$ of 2,6-DMN in the overall process, or to decrease the purity of 2,6-DMN obtained by separation in the crystallization step. These conditions are extremely disadvantageous for commercial practice.

According to the present invention, however, these complicated and troublesome conditions can be avoided by using a starting material in the isomerization step in which the connection of 2,6-DMN in the total feed is less than the thermodynamic equilibrium concentration, and the weight ratio of DMN of group A to DMN not belonging to group A is maintained at not less than 12. Thus, there is no necessity of avoiding the intermolecular rearrangement, and minimizing the amount of DMN not belonging to group A in the starting material. In addition, it is possible to increase the yield $[(\eta_{26})_T(\%)]$ of 2,6-DMN in the overall process, and to increase the purity of 2,6-DMN obtainable by separation in the crystallization step. Furthermore, the present invention can be performed with greater commercial advantage by maintaining the above weight ratio of DMN of group A to DMN not belonging to group A at 1.4 to 8, especially at 2.2 to 6.

If the contents of low boiling and high boiling components other than DMN in the isomerization reaction material (for example, MMN or TMN are increased, the yield $[(\eta_{26})_c(\%)]$ of 2,6-DMN in the crystallization step is decreased, or the proportion of DMN not belonging to group A formed in the isomerization reaction increases. Accordingly, it is better to reduce the contents of the low boiling and high boiling components in the material. The content of TMN should be reduced to not more than 10% by weight, preferably to not more than 5% by weight, and the concentration of low boiling and high boiling components other than DMN (such as MMN and TMN) should be not more than 20% by weight, preferably not more than 10% by weight.

In the present application, the term "low boiling component" denotes those components which have a boiling point lower than the lowest boiling DMN isomer among the 10 isomers, and the term "high boiling components" means those compounds which have a boiling point higher than the highest boiling DMN isomer among the 10 isomers.

Another new aspect of the process of this invention is that the weight percent $C_{26}$ of the reaction product should satisfy the following equation:

$$C_{26} = \frac{2,6\text{-DMN (weight)}}{2,6\text{-DMN (weight)} + 1,6\text{-DMN (weight)} + 1,5\text{-DMN (weight)}} \times 100\%$$
$$\geq 27 \text{ (wt.\%)}$$

preferably $$31.5 \leq C_{26} \text{ (wt.\%)} \leq 46.5$$

especially preferably $$36 \leq C_{26} \text{ (wt.\%)} \leq 44.5$$

and the disproportionation ratio D (% by weight) of dimethylnaphthalenes not belonging to group A and the ratio G (% by weight) of dimethylnaphthalenes not belonging to group A formed from DMN of group A should satisfy the following equation $$D \leq -0.90G + 6.76 \text{ (\% by weight)}$$

preferably $$D \leq -0.80G + 5.0 \text{ (\% by weight)}$$

especially preferably $$D \leq -0.56G + 2.8 \text{ (\% by weight)}.$$

If these conditions are not met, the yield $[(\eta_{26})_T (\%)]$ of 2,6-DMN in the overall process and/or the rate of recovery $[(\eta_{26})_C (\%)]$ in the crystallization step have to be reduced remarkably.

The method of separating 2,6-DMN from the isomerization reaction product in the crystallization step is not particularly limited. For example, 2,6-DMN of the desired purity can be obtained by crystallizing 2,6-DMN at a temperature higher than the temperature at which it forms a eutectic mixture together with other naphthalene compounds without adding any other solvent to the reaction product, and if the purity of the resulting 2,6-DMN is lower than the desired purity, repeating further crystallization and/or washing until 2,6-DMN of the desired purity is obtained. Furthermore, in the crystallization step, high purity 2,6-DMN can also be obtained by using a purification method using a known solvent, for example, alcohols such as methanol, aromatic hydrocarbons such as xylene, or aliphatic hydrocarbons such as hexane. For commercial operation, the method comprising crystallizing 2,6-DMN without adding another solvent, at a temperature higher than the temperature at which it forms a eutectic mixture, is preferred.

The residue resulting from the separation of 2,6-DMN in the crystallization step is recycled, and again used as part of the reaction material to be fed into the isomerization reaction step. At this time, a part of the residue can be returned to the crystallization step for the purpose of controlling the concentration of the slurry.

In order to produce high purity 2,6-DMN at a high yield and with commercial advantage in accordance with the present invention, it is preferred to operate the process so that the amount of substances withdrawn out of the reaction system by purging and/or distillation (excluding 2,6-DMN withdrawn as a product) satisfies the following relation with respect to the amounts of the material to be freshly fed into the reaction system and the dimethylnaphthalenes of group A contained in the material $$\frac{P - (F - F_A)}{F_A} \leq 0.20$$

wherein P is the weight of substances to be withdrawn out of the reaction system (excluding 2,6-DMN withdrawn as a product), F is the total weight of the material to be fed freshly into the reaction system, and $F_A$ is the weight of dimethylnaphthalenes of group A contained in the material.

More preferably $$\frac{P - (F - F_A)}{F_A} \leq 0.15$$

and especially preferably $$\frac{P - (F - F_A)}{F_A} \leq 0.10$$

If the amount of the above substances to be withdrawn out of the reaction system is increased beyond the above limitation, it is impossible to accumulate dimethylnaphthalenes not belonging to group A in the reaction system in sufficient amounts, and it becomes difficult to produce high purity 2,6-DMN in a high yield and with commercial advantage.

The following Examples further illustrate the present invention in greater detail.

In these Examples, all parts are by weight unless otherwise specified.

The "isomerization reaction material" means a material to be introduced into the isomerization reaction zone. Accordingly, when the process follows the flow chart shown in FIG. 2, it means a mixture of the recycle material and a freshly fed material. When the process follows the flow chart shown in FIG. 1, the isomerization reaction material means one obtained by removing components having a higher or lower boiling point than DMN from a mixture of the recycle material and a freshly fed material.

S. V. expresses the weight (Kg) of DMN fed as an isomerization reaction material per kilogram of the catalyst per hour.

Measurement of D

1. Using the reaction apparatus which is the same as or similar to that used in each of the following Examples, an isomerization reaction material of the same composition was reacted at the same temperature and pressure as in each of the Examples. When a carrier gas or diluent was used, its kind and its proportion to the isomerization reaction material were made the same as in each of the Examples. The reaction was performed while varying S. V. and the S. V. at which the value of $C_{26}$ became equal to that in each of the Examples was determined.

2. An isomerization reaction material of the composition obtained by replacing the DMN of group A in the isomerization reaction material used in (1) above with DMN not belonging to group A (the proportions of the isomers in the DMN not belonging to group A were made equal to those of the DMN not belonging to group A and used in (1) above) was isomerized in the same way as in (1) above except that S. V. was adjusted to that determined in (1) above.

3. The amount of components other than DMN in the isomerization reaction material was compared with that of components other than DMN in the product, and D was defined as the weight percent of the increase of the amount of components other than DMN in the product over that of components other than DMN in the isomerization reaction material, based on the amount of DMN not belonging to group A which was present in the starting material.

Measurement of G

1. The same procedures as in (1) and (2) in the measurement of D were followed except that in procedure (2), the DMN not belonging to group A in the isomerization reaction material was replaced by DMN of group A instead of replacing the latter with the former.

2. G was defined as the weight percent of DMN not belonging to group A and contained in the reaction product, based on the amount of DMN of group A in the starting material.

$(\eta_{26})_T\%$ was calculated in the following manner.

$$\frac{\text{Weight of 2,6-DMN in the product}}{\text{Weight of DMN of group } A \text{ in the material to be freshly supplied to the system}} \times 100 \text{ (wt.\%)}$$

The values shown in the tables below were those obtained when the process was operated in a steady state.

EXAMPLES 1 AND 2

Each of the isomerization reaction materials shown in Table 1 was isomerized using the catalyst shown in Table 1 by a vapor phase reaction using nitrogen gas as a carrier gas in accordance with the flow chart shown in FIG. 1. The resulting product was treated in the crystallization step so that 2,6-DMN did not form a eutectic mixture together with ether naphthalene compounds. The 2,6-DMN precipitated was separated, and collected. The residue was mixed with 100 parts/hour of a material to be freshly fed into the reaction system. In the distillation step, components having lower boiling points than DMN (for example, MMN; to be abbreviated as LE) and components having higher boiling points than DMN (for example, TMN; to be abbreviated as HE) were withdrawn out of the system, and the remainder was recycled.

The yield and purity of the resulting 2,6-DMN were both high, and fully satisfactory. The reaction conditions and the results obtained are shown in Table 1.

The material to be freshly fed into the system had the following composition.

| | |
|---|---|
| LE | 10.4% by weight |
| 2,6-DMN | 0 |
| 1,6-DMN | 0.5% by weight |
| 1,5-DMN | 86.6% by weight |
| 2,7-DMN 1,7-DMN 1,8-DMN | 1.0% by weight |
| other DMN | 0 |
| HE | 1.5% by weight |

COMPARATIVE EXAMPLE 1

This example shows the consequence of reducing the $C_{26}$ value of the isomerization reaction product to below 27 (outside the scope of this invention).

Example 1 was repeated except that the reaction conditions and the isomerization reaction material shown in Table 1 were used. The resulting 2,6-DMN had low purity, and the flow rate of the recycle system was very large. This process was commercially disadvantageous. The results are shown in Table 1.

The amount and composition of the material to be freshly fed into the system were the same as in Example 1.

EXAMPLE 3

Example 1 was repeated except that the isomerization catalyst, the isomerization reaction material, and the conditions shown in Table 1 were used. The yield and purity of the resulting 2,6-DMN were both high, and satisfactory. The conditions and the results are shown in Table 1.

The amount and composition of the material to be fed freshly into the reaction system were the same as in Example 1.

COMPARATIVE EXAMPLE 2

This example shows the consequence of choosing D and G outside the range specified in the present invention (D ≦ −0.9G + 6.67).

Example 3 was repeated except that the reaction conditions and the isomerization reaction material shown in Table 1 were used. The yield of the resulting 2,6-DMN was extremely low, and the process was commercially disadvantageous. The results are shown in Table 1.

The flow rate and composition of the material to be fed freshly into the system were the same as in Example 1.

EXAMPLE 4

Example 1 was repeated except that an isomerization catalyst composed of 15% by weight of bentonite and 85% by weight of the hydrogen form of mordenite with 0.5% by weight of platinum supported thereon was used, a hydrogen was used as carrier gas, and the reaction conditions and the isomerization reaction material shown in Table 1 were used. The results are shown in Table 1.

The yield and purity of the resulting 2,6-DMN were both high, and satisfactory. The flow rate and composition of the material to be fed freshly into the system were the same as in Example 1.

COMPARATIVE EXAMPLES 3 and 4

These examples show the case in which the weight ratio of DMN of group A to DMN belonging to group A was greater than that specified in the present invention.

The isomerization reaction material shown in Table 1 was used, and 2,7-DMN was removed out of the system as a eutectic mixture from the residue resulting from the crystallization and separation of 2,6-DMN from the isomerization reaction. The remainder was recycled and the weight ratio of DMN of group A to DMN not belonging to group A in the material to be fed into the reaction zone was maintained as indicated in Table 1. Otherwise, the process was operated in the same way as in Example 4. The results are shown in Table 1.

The yield of the resulting 2,6-DMN was markedly low as compared with that in Example 4, and the purity of the product was somewhat lower than in Example 4. The flow rate and composition of the material to be freshly fed into the system were the same as in Example 1. The amount of the 2,7-DMN eutectic mixture removed from the residue to be recycled was 27.4 parts (Comparative Example 3), and 25.7 parts (Comparative Example 4).

EXAMPLE 5

Example 1 was repeated except that no diluent was used, and the isomerization reaction was conducted in the liquid phase under the reaction conditions shown in Table 1. The yield and purity of the resulting 2,6-DMN were both high, and satisfactory. The results are shown in Table 1.

The flow rate and composition of the material to be freshly fed into the system were the same as in Example 1.

Table 1

| | Catalyst | Temperature (°C) | Pressure (kg/cm²G) | Partial pressure of DMN (kg/cm²) | S.V. (kg/kg.hr) | 2,6-DMN | 1,6-DMN | 1,5-DMN | DMN of group B | Other DMN | LE | HE | Weight ratio of DMN of group A to DMN not belonging to group A |
|---|---|---|---|---|---|---|---|---|---|---|---|---|---|
| Ex. 1 | A | 320 | 0.5 | 0.45 | 0.4 | 11.0 | 27.6 | 33.4 | 25.4 | 0.9 | 1.2 | 0.5 | 2.73 |
| Ex. 2 | A | 300 | 0.8 | 0.4 | 0.3 | 11.0 | 26.2 | 35.0 | 25.3 | 0.9 | 1.1 | 0.5 | 2.75 |
| Com. Ex. 1 | A | 280 | 0.6 | 0.2 | 0.7 | 20.1 | 26.1 | 40.0 | 13.4 | 0.2 | 0.1 | 0.1 | 6.34 |
| Ex. 3 | B | 320 | 0.5 | 0.2 | 0.6 | 10.0 | 32.3 | 30.4 | 23.2 | 1.3 | 1.9 | 0.9 | 2.97 |
| Com. Ex. 2 | B | 340 | 0.5 | 1.2 | 0.7 | 9.5 | 28.6 | 32.7 | 18.3 | 2.2 | 5.5 | 3.2 | 3.45 |
| Ex. 4 | C | 400 | 10 | 1.0 | 2.5 | 12.4 | 30.3 | 24.7 | 29.4 | 1.1 | 1.4 | 0.7 | 2.21 |
| Com. Ex. 3 | C | 400 | 10 | 1.0 | 2.3 | 1.3 | 37.0 | 53.5 | 4.7 | 0.2 | 2.4 | 0.9 | 18.7 |
| Com. Ex. 4 | C | 400 | 10 | 1.0 | 2.3 | 1.8 | 36.9 | 51.5 | 6.2 | 0.1 | 2.9 | 0.6 | 14.3 |
| Ex. 5 | A | 290 | 6 | — | 1.5 | 9.7 | 31.8 | 36.4 | 19.0 | 0.8 | 1.6 | 0.7 | 3.94 |

| | Catalyst | $C_{26}$ (wt.%) | D (wt.%) | G (wt.%) | $\frac{P-(F-F_A)}{F_A}$ |
|---|---|---|---|---|---|
| Ex. 1 | A | 41.9 | 0.8 | 0.3 | 0.0344 |
| Ex. 2 | A | 38.3 | 0.41 | 0.1 | 0.0185 |
| Com. Ex. 1 | A | 24.8 | 0.04 | 0.01 | 0.0343 |
| Ex. 3 | B | 40.5 | 2.0 | 1.0 | 0.0877 |
| Com. Ex. 2 | B | 40.5 | 9.0 | 4.0 | 0.331 |
| Ex. 4 | C | 44.1 | 1.4 | 1.3 | 0.0698 |
| Com. Ex. 3 | C | 44.1 | 1.4 | 1.3 | 0.323 |
| Com. Ex. 4 | C | 44.1 | 1.4 | 1.3 | 0.306 |
| Ex. 5 | A | 40.5 | 1.4 | 0.2 | 0.0542 |

Results:

| Flow rate of the isomerization reaction material | 2,6-DMN obtained as product | Weight ratio of the material to be freshly fed into the system to 2,6-DMN as | Weight ratio of the isomerization reaction material to 2,6-DMN as product | 2,6-DMN as product Purity | Yield $(\eta 26)T$ |
|---|---|---|---|---|---|

Table 1-continued

|   | (Parts/hr.) | (parts/hr.) | product |  | (wt.%) | (%) |
|---|---|---|---|---|---|---|
| Ex. 1 | 442 | 84.1 | 1.19 | 5.25 | 99.0 | 95.6 |
| Ex. 2 | 512 | 85.5 | 1.17 | 5.99 | 98.5 | 96.6 |
| Com. Ex. 1 | 6680 | 84.1 | 1.19 | 79.4 | 94.0 | 90.6 |
| Ex. 3 | 419 | 79.5 | 1.26 | 5.28 | 98.5 | 89.8 |
| Com. Ex. 2 | 360 | 58.3 | 1.72 | 6.18 | 98.0 | 65.6 |
| Ex. 4 | 479 | 81.0 | 1.23 | 5.91 | 99.0 | 92.1 |
| Com. Ex. 3 | 170 | 59.0 | 1.69 | 2.88 | 95.5 | 64.7 |
| Com. Ex. 4 | 182 | 60.5 | 1.65 | 3.00 | 98.0 | 68.1 |
| Ex. 5 | 383 | 82.4 | 1.21 | 4.65 | 99.2 | 93.8 |

Note:
Catalyst A stands for composition composed of 85 wt.% of hydrogen form of mordenite and 15 wt.% of fuller's earth
Catalyst B stands for silica-alumina $SiO_2/Al_2O_3 = 72/28$ (weight ratio)
Catalyst C stands for composition composed of 85 wt.% of hydrogen form of mordenite containing 0.5 wt.% of platinum and 15 wt.% of bentonite.

EXAMPLE 6 TO 10

In accordance with the flow chart shown in FIG. 2, the isomerization reaction was performed under the conditions shown in Table 2 using the catalyst shown in Table 2 in the liquid phase without using a diluent.

The reaction product was distilled to remove components having lower and higher boiling points than DMN out of the system. The residue was treated in the crystallization step under conditions which induced the crystallization of 2,6-DMN alone. In this case, only 2,6-DMN was first precipitated. The precipitated 2,6-DMN was separated, and collected. The residue was 100 parts/hour of a material to be fed freshly into the system, and recycled.

The yield and purity of the resulting 2,6-DMN were both high, and fully satisfactory. The conditions and the results are shown in Table 2.

The composition of the material to be fed freshly into the reaction system was as follows:

| LE | 9.9% by weight |
|---|---|
| 2,6-DMN | 0 |
| 1,6-DMN | 3.6% by weight |
| 1,5-DMN | 84.0% by weight |
| 2,7-DMN<br>1,7-DMN<br>1,8-DMN | 1.0% by weight |
| other DMN | 0 |
| HE | 1.5% by weight |

COMPARATIVE EXAMPLE 5

This example shows the consequence of choosing the relation between D and G outside the scope of the present invention ($D \leq -0.9G + 6.76$).

The isomerization reaction was carried out in the vapor phase in accordance with the same flow as in Example 7 using nitrogen as a carrier gas. The catalyst used was the same as that in Example 7, and the reaction conditions used were those shown in Table 2. The yield of the resulting 2,6-DMN was low, and the process was commercially disadvantageous. The results are shown in Table 2.

The flow rate and composition of the material to be fed freshly into the system were the same as in Example 7.

COMPARATIVE EXAMPLE 6

This example also shows the consequence of choosing the relation between D and G outside the range specified in the present invention ($D \leq -0.9G + 6.76$).

The isomerization reaction was carried out in accordance with the same flow as in Example 6 in the vapor phase using nitrogen as a carrier gas. The catalyst used was the same as that used in Example 1, and the reaction conditions used were those shown in Table 2. The yield of the resulting 2,6-DMN was low, and the process was commercially disadvantageous. The results are shown in Table 2.

The flow rate and composition of the material to be fed freshly into the system were the same as in Example 6.

EXAMPLE 11

The isomerization reaction was carried out in the vapor phase using hydrogen as a carrier gas in accordance with the same flow as in Example 6. The catalyst used was the same as that used in Example 4, and the reaction conditions used were those shown in Table 2. The yield and purity of the resulting 2,6-DMN were both high, and fully satisfactory. The results are shown in Table 2.

The flow rate and composition of the material to be freshly fed into the system were the same as in Example 6.

EXAMPLE 12

Example 6 was repeated except that the catalyst and the conditions shown in Table 2 were used. The yield and purity of the resulting 2,6-DMN were both high and fully satisfactory. The conditions and the results are shown in Table 2.

The flow rate and composition of the material to be freshly fed into the system were the same as in Example 6.

EXAMPLE 13

The isomerization reaction was performed in accordance with the flow shown in FIG. 2 in the liquid phase without using a diluent. The catalyst and the conditions as shown in Table 2 were employed. The yield and purity of the resulting 2,6-DMN were both high, and fully satisfactory. The results are shown in Table 2.

The flow rate of a material to be freshly fed into the reaction system was 100 parts/hour, and its composition was as follows:

| | |
|---|---|
| LE | 5.4% by weight |
| 2,6-DMN | 1.0% by weight |
| 1,6-DMN | 8.9% by weight |
| 1,5-DMN | 75.2% by weight |
| 2,7-DMN <br> 1,7-DMN <br> 1,8-DMN | 8.0% by weight |
| other DMN | 0 |
| HE | 1.5% by weight |

Table 2

| | | Reaction condition | | | | | | | | | |
|---|---|---|---|---|---|---|---|---|---|---|---|
| | | | | | Isomerization reaction material | | | | | | |
| | | | | | Composition (wt.%) | | | | | | Weight ratio of DMN of group A to DMN not belonging to group A |
| | Catalyst | Temperature (°C) | Pressure (kg/cm²G) | Partial pressure of DMN (kg/cm²) | S.V. (kg/kg·hr) | 2,6-DMN | 1,6-DMN | 1,5-DMN | DMN of group B | Other DMN | LE | HE | |
| Ex. 6 | D | 280 | 3.0 | — | 1.9 | 9.5 | 30.8 | 32.7 | 22.0 | 0.2 | 4.1 | 0.7 | 3.29 |
| Ex. 7 Com. | E | 280 | 3.5 | — | 1.9 | 8.5 | 32.4 | 37.2 | 13.8 | 0.4 | 5.6 | 2.1 | 5.50 |
| Ex. 5 | E | 275 | 1.5 | 0.15 | 0.9 | 5.7 | 27.8 | 44.5 | 13.1 | 0.1 | 6.4 | 2.4 | 5.91 |
| Ex. 8 | F | 270 | 3.0 | — | 1.4 | 9.0 | 31.6 | 35.7 | 17.3 | 0.4 | 4.7 | 1.3 | 4.31 |
| Ex. 9 | G | 330 | 4.0 | — | 0.5 | 9.2 | 31.4 | 36.7 | 14.8 | 0.5 | 5.2 | 2.2 | 5.05 |
| Ex. 10 Com. | H | 280 | 2.5 | — | 1.9 | 10.0 | 29.8 | 32.0 | 23.2 | 0.3 | 3.9 | 0.8 | 3.06 |
| Ex. 6 | A | 450 | 1.2 | 0.4 | 0.7 | 10.7 | 27.7 | 28.8 | 25.0 | 0.5 | 5.8 | 1.5 | 2.64 |
| Ex. 11 | C | 430 | 10 | 1.5 | 3.8 | 15.5 | 24.9 | 16.9 | 36.7 | 0.9 | 3.3 | 1.8 | 1.52 |
| Ex. 12 | I | 350 | 8 | — | 1.8 | 8.6 | 30.8 | 32.3 | 19.8 | 0.4 | 5.9 | 2.2 | 3.55 |
| Ex. 13 | I | 310 | 4 | — | 1.5 | 15.7 | 25.2 | 17.7 | 37.8 | 0.5 | 1.8 | 1.3 | 1.53 |

| | | Reaction Condition | | | |
|---|---|---|---|---|---|
| | Catalyst | $C_{26}$ (wt.%) | D (wt.%) | G (wt.%) | $\dfrac{P-(F-F_A)}{F_A}$ |
| Ex. 6 | D | 41.0 | 0.9 | 0.2 | 0.0331 |
| Ex. 7 Com. | E | 41.0 | 3.2 | 0.3 | 0.104 |
| Ex. 5 | E | 47.7 | 21.0 | 4.2 | 0.446 |
| Ex. 8 | F | 40.1 | 2.0 | 0.3 | 0.0719 |
| Ex. 9 | G | 39.6 | 3.0 | 0.4 | 0.106 |
| Ex. 10 Com. | H | 40.5 | 1.0 | 0.2 | 0.0400 |
| Ex. 6 | A | 45.0 | 5.8 | 3.6 | 0.226 |
| Ex. 11 | C | 45.9 | 1.4 | 3.5 | 0.105 |
| Ex. 12 | I | 46.4 | 4.2 | 1.5 | 0.129 |
| Ex. 13 | I | 42.8 | 2.4 | 0.35 | 0.125 |

| | Results | | | | | |
|---|---|---|---|---|---|---|
| | Flow rate of the isomerization reaction material (Parts/hr.) | 2,6- obtained as product (Parts/hr.) | Weight ratio of the material to by freshly fed into the system to 2,6-DMN as product | Weight ratio of the isomerization reaction material to 2,5-DMN as product | 2,6-DMN as product | |
| | | | | | Purity (wt.%) | Yield $(\eta_{26})_T$ (%) |
| Ex. 6 | 416 | 84.7 | 1.18 | 4.91 | 98.5 | 95.2 |

Table 2-continued

| | | | | | | |
|---|---|---|---|---|---|---|
| Ex. 7 | 348 | 78.5 | 1.27 | 4.43 | 99.0 | 88.7 |
| Com. Ex. 5 | 210 | 48.5 | 2.06 | 4.33 | 97.6 | 54.0 |
| Ex. 8 | 385 | 81.3 | 1.23 | 4.74 | 98.7 | 91.7 |
| Ex. 9 | 379 | 78.3 | 1.28 | 4.84 | 98.6 | 88.1 |
| Ex. 10 | 445 | 84.1 | 1.19 | 5.29 | 99.2 | 95.2 |
| Com. Ex. 6 | 386 | 67.8 | 1.48 | 5.69 | 97.8 | 75.7 |
| Ex. 11 | 756 | 78.4 | 1.28 | 9.64 | 98.6 | 88.3 |
| Ex. 12 | 327 | 76.3 | 1.31 | 4.29 | 98.5 | 85.8 |
| Ex. 13 | 825 | 74.5 | 1.34 | 11.1 | 98.5 | 87.2 |

Note:
Catalysts A and C are the same as in Table 1.
Catalyst D stands for composition composed of 15 wt.% of fuller's earth and 85 wt.% of hydrogen form of mordenite containing 0.5 wt.% of Cr.
Catalyst E stands for Y-type zeolite containing rare earths (Linde SK-500)
Catalyst F stands for Y-type zeolite containing manganese (Linde SK-110)
Catalyst G stands for X-type zeolite containing 5% by weight of Mn
Catalyst H stands for composition consisting of 85 wt.% of H-form mordenite containing 0.5 wt.% of Bi, and 15 wt.% of fuller's earth.
Catalyst I stands for composition composed of 11 wt.% of bentonite and 85 wt.% of H-form of mordenite.

EXAMPLES 14 to 16

The isomerization reaction was carried out in accordance with the flow shown in FIG. 2 in the liquid phase without using a diluent. The catalyst and the conditions shown in Table 3 were employed. The yield and purity of the resulting 2,6-DMN were both high, and fully satisfactory. The results are shown in Table 3.

The flow rate of a material to be freshly fed into the reaction system was 100 parts per hour, and its composition was as follows:

| | |
|---|---|
| LE | 9.9% by weight |
| 2,6-DMN | 0 |
| 1,6-DMN | 3.6% by weight |
| 1,5-DMN | 84.5% by weight |
| 2,7-DMN, 1,7-DMN, 1,8-DMN | 0.5% by weight |
| other DMN | 0 |
| HE | 1.5% by weight |

EXAMPLE 17

The isomerization reaction was carried out in accordance with the flow shown in FIG. 1 in the gaseous phase using hydrogen as a carrier gas. The catalyst used was the same as that used in Example 4, and the reaction conditions used were those shown in Table 3. The yield and purity of the resulting 2,6-DMN were both high, and fully satisfactory. The results are shown in Table 3.

The flow rate and composition of the material to be fed freshly into the reaction system were the same as in Example 1.

EXAMPLE 18

Example 1 was repeated except that in accordance with the flow shown in FIG. 1, a part of the residue resulting from the separation of 2,6-DMN in the crystallization step was purged out of the system, and the remainder was mixed with the material freshly fed into the system (therefore, the composition of the isomerization reaction material changed). The reaction conditions and the results are shown in Table 3.

The yield of the resulting 2,6-DMN was somewhat lower than in Example 1, but since the amount of the recycle flow could be reduced, the process was fully satisfactory for commercial operation. The amount of the residue purged out of the system was 2.7 parts/hour.

Table 3

| | Reaction condition | | | | | | | | | | Weight ratio of DMN of group A to DMN not belonging to group A |
|---|---|---|---|---|---|---|---|---|---|---|---|
| | Catalyst | Temperature (°C) | Pressure (kg/cm²G) | Partial pressure of DMN (kg/cm²) | S.V. (kg/kg·hr) | Isomerization reaction material Composition (wt.%) | | | | | |
| | | | | | | 2,6-DMN | 1,6-DMN | 1,5-DMN | DMN of group B | Other DMN | LE | HE | |
| Ex. 14 | I | 310 | 4 | — | 1.9 | 10.8 | 33.5 | 39.0 | 11.4 | 0.3 | 4.2 | 0.8 | 7.12 |
| Ex. 15 | I | 310 | 4 | — | 2.4 | 14.0 | 31.2 | 40.3 | 10.4 | 0.2 | 3.3 | 0.6 | 8.07 |
| Ex. 16 | E | 280 | 3.5 | — | 3.3 | 14.5 | 31.1 | 42.0 | 7.5 | 0.3 | 3.6 | 1.0 | 11.2 |
| Ex. 17 | C | 420 | 10 | 0.8 | 3.4 | 13.8 | 24.5 | 26.9 | 32.9 | 0.3 | 1.3 | 0.3 | 1.96 |
| Ex. 18 | A | 320 | 0.5 | 0.45 | 0.4 | 9.4 | 29.9 | 39.5 | 18.5 | 0.6 | 1.7 | 0.4 | 4.13 |

Table 3-continued

| | Catalyst | Reaction Condition | | | |
|---|---|---|---|---|---|
| | | $C_{26}$ (wt.%) | D (wt.%) | G (wt.%) | $\frac{P-(F-F_A)}{F_A}$ |
| Ex. 14 | I | 38.3 | 1.3 | 0.08 | 0.0522 |
| Ex. 15 | I | 35.1 | 0.92 | 0.03 | 0.0488 |
| Ex. 16 | E | 35.1 | 1.5 | 0.03 | 0.0772 |
| Ex. 17 | C | 40.7 | 1.0 | 1.3 | 0.0712 |
| Ex. 18 | A | 41.9 | 0.8 | 0.3 | 0.0552 |

| | Results | | | 2,6-DMN as product | |
|---|---|---|---|---|---|
| | Flow rate of the isomerization reaction material (Parts/hr.) | 2,6- obtained as product (parts/hr.) | Weight ratio of the material to be freshly fed into the system to 2,6-DMN as product | Weight ratio of the isomerization reaction material to 2,6-DMN as product | Purity (wt.%) | Yield $(\eta_{26})_T$ (%) |
| Ex. 14 | 402 | 83.5 | 1.20 | 4.81 | 98.9 | 93.8 |
| Ex. 15 | 526 | 83.8 | 1.19 | 6.28 | 98.9 | 94.0 |
| Ex. 16 | 508 | 81.3 | 1.23 | 6.25 | 98.5 | 90.9 |
| Ex. 17 | 649 | 80.9 | 1.24 | 8.02 | 98.7 | 91.6 |
| Ex. 18 | 352 | 82.3 | 1.22 | 4.28 | 99.1 | 93.6 |

Note:
Catalysts A, C, E and I are the same as in Table 1 and 2.

What we claim is:

1. In a process for preparing 2,6-dimethylnaphthalene by the selective isomerization of a dimethylnaphthalene (DMN) mixture, which comprises a step of isomerizing a mixture of dimethylnaphthalenes in the presence of a solid acid catalyst, a crystallization step of separating 2,6-dimethylnaphthalene from the resulting isomerized reaction mixture, and a distillation step of separating components having lower or higher components than dimethylnaphthalenes contained in the dimethylnaphthalene mixture at any desired stage of the process with the residue from the crystallization step being recycled to the isomerization step for use as part of the starting material; the improvement comprising:

1. the concentration of 2,6-dimethylnaphthalene in the isomerization reactant for the isomerization reaction is less than the thermodynamic equilibrium concentration, and the weight ratio of dimethylnaphthalenes of group A consisting of 2,6-dimethylnaphthalene (2,6-DMN), 1,6-dimethylnaphthalene (1,6-DMN), and 1,5-dimethylnaphthalene (1,5-DMN) to the dimethylnaphthalenes not belonging to group A is defined by the following equation $$\frac{\text{Weight of DMN of group } A}{\text{Weight of DMN not belonging to group } A} \leq 12$$

2. in the isomerization reaction, the concentration $C_{26}$ of 2,6-dimethylnaphthalene in the reaction product expressed in percent by weight based on the dimethylnaphthalenes of group A satisfies the following equation $$C_{26} = \frac{2,6\text{-DMN (weight)}}{2,6\text{-DMN (weight)} + 1,6\text{-DMN (weight)} + 1,5\text{-DMN (weight)}} \times 100 \geq 27 \text{ (weight \%)}$$

and the disproportionation ratio D of DMN not belonging to group A, having the following definition:

$$D = \frac{\text{Weight of by-products other than DMN, formed from DMN not belonging to group } A}{\text{Weight of DMN not belonging to group } A \text{ which is contained in the isomerization reactant}} \times 100 \text{ (wt.\%)}$$

and the conversion G, defined as:

$$G = \frac{\text{Weight of DMN not belonging to group } A \text{ formed from DMN of group } A}{\text{Weight of DMN of group } A \text{ contained in the isomerization reactant}} \times 100 \text{ (wt.\%)}$$

satisfy the following equation $$D \leq -0.9G + 6.76 \text{ (wt.\%)}$$

2. The process of claim 1 wherein $$31.5 \leq C_{26} \text{ (wt.\%)} \leq 46.6$$

3. The process of claim 2 wherein $$36 \leq C_{26} \text{ (wt.\%)} \leq 44.5$$

4. The process of claim 1 wherein $$D \leq -0.80G + 5.0 \text{ (wt.\%)}$$

5. The process of claim 4 wherein $$D \leq -0.56G + 2.8 \text{ (wt.\%)}$$

6. The process of claim 1 wherein: P, the amount of substances withdrawn from the reaction system exclusive of the product 2,6-DMN; F, the amount of the total weight of the material to be freshly fed into the reaction system; and $F_A$, the amount of dimethylnaphthalenes of group A contained in the material, satisfy the following relation:

$$\frac{P - (F - F_A)}{F_A} \leq 0.20.$$

7. The process of claim 6 wherein $$\frac{P - (F - F_A)}{F_A} \leq 0.15.$$

8. The process of claim 7 wherein $$\frac{P - (F - F_A)}{F_A} \leq 0.10.$$

9. The process of claim 1 wherein the weight ratio $$\frac{\text{Weight of DMN of group } A}{\text{Weight of DMN not belonging to group } A}$$

has a value of from 1.4 to 8.

10. The process of claim 9 wherein the weight ratio has a value of from 2.2 to 6.

* * * * *